United States Patent [19]

Broecker et al.

[11] Patent Number: 4,780,448
[45] Date of Patent: Oct. 25, 1988

[54] PREPARATION OF A CATALYST CONTAINING COPPER AND SILICA

[75] Inventors: Franz J. Broecker, Ludwigshafen; Rolf Fischer, Heidelberg; Klaus-Dieter Malsch, Schifferstadt; Wolfgang Reiss, Ludwigshafen; Rolf Schnabel, Schifferstadt; Hans-Martin Weitz, Bad Durkheim, all of Fed. Rep. of Germany

[73] Assignee: BASF Aktiengesellschaft, Ludwigshafen, Fed. Rep. of Germany

[21] Appl. No.: 14,072

[22] Filed: Jan. 30, 1987

Related U.S. Application Data

[63] Continuation of Ser. No. 821,447, Jan. 22, 1986, abandoned.

[30] Foreign Application Priority Data

Feb. 2, 1985 [DE] Fed. Rep. of Germany ....... 3503587

[51] Int. Cl.$^4$ .......................... B01J 21/08; B01J 21/18
[52] U.S. Cl. ..................................... 502/244; 502/243; 502/174; 502/201
[58] Field of Search ................ 502/174, 201, 243, 244

[56] References Cited

U.S. PATENT DOCUMENTS

| | | | |
|---|---|---|---|
| 3,494,734 | 2/1970 | Nokamura | 502/201 X |
| 3,756,964 | 9/1973 | Frazee et al. | 502/60 X |
| 4,536,491 | 8/1985 | Fremont | 502/174 |

FOREIGN PATENT DOCUMENTS

| | | | |
|---|---|---|---|
| 0020048 | 5/1979 | European Pat. Off. | 502/244 |
| 64241 | 4/1982 | European Pat. Off. | |
| 2538253 | 8/1975 | Fed. Rep. of Germany | 502/244 |
| 2256780 | 1/1974 | France | 502/244 |
| 55-66541 | 3/1978 | Japan | 502/244 |
| 57-122938 | 1/1981 | Japan | 502/244 |
| 59-32949 | 8/1982 | Japan | 502/244 |
| 910178 | 7/1980 | U.S.S.R. | 502/244 |

*Primary Examiner*—Andrew H. Metz
*Assistant Examiner*—William G. Wright
*Attorney, Agent, or Firm*—John H. Shurtleff

[57] ABSTRACT

A catalyst containing copper and silica is prepared by a process in which an aqueous alkali metal silicate solution containing from 1 to 26% by weight of $SiO_2$ is brought to a pH of from 0.5 to 2.0 with nitric acid, an aqueous copper nitrate solution containing from 5 to 15% by weight of Cu is added, after the addition of the nitric acid, so that a clear solution containing from 0.18 to 3.0 moles of Cu per mole of $SiO_2$ is formed, the resulting solution is mixed with an aqueous alkali metal carbonate solution at from 40° to 80° C., the pH of the mixture being kept at from 7.5 to 8.5, and the precipitated material is separated off, dried, calcined by heating at from 250° to 400° C. and pressed in a conventional manner to give catalyst moldings. The catalyst thus obtained is used for the hydrogenation of dialkyl dicarboxylates to diols.

6 Claims, 1 Drawing Sheet

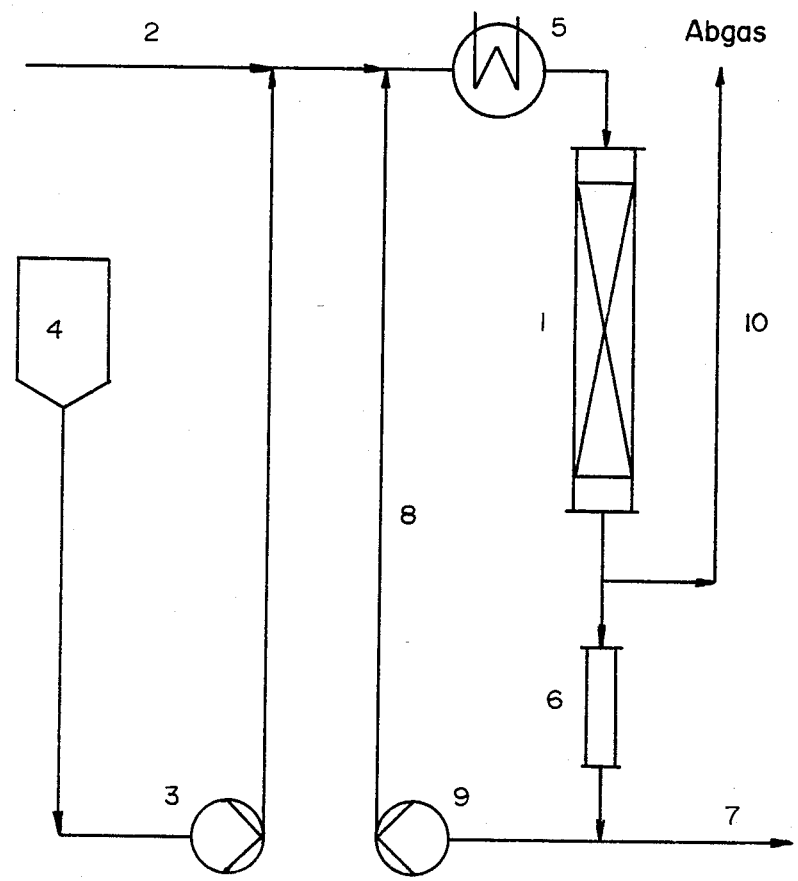

PREPARATION OF A CATALYST CONTAINING COPPER AND SILICA

This application is a continuation of application Ser. No. 821,447 filed Jan. 22, 1986, now abandoned.

The present invention relates to a process for the preparation of a catalyst containing copper and silica, and the use of the catalyst thus prepared for the hydrogenation of dialkyl dicarboxylates to diols.

Catalysts containing copper and silica and their suitability for hydrogenation of ketones, aldehydes and carboxylates are known. For example, U.S. Pat. No. 3,756,964 describes a catalyst which is prepared by impregnation of an inorganic oxide, such as silica gel, with solutions of copper salts and chromic acid, and stepwise heating. A copper catalyst which is useful for hydrogenating diesters of oxalic acid to glycol is described in European Pat. No. 64,241. This catalyst is prepared by combining an amine complex of copper with colloidal silica gel. Japanese Patent Application No. 45 337/1972 describes a process for the preparation of γ-butyrolactone, in which the esters of the corresponding dicarboxylic acids are hydrogenated in the presence of a catalyst which consists of from 10 to 70% by weight of copper, from 5 to 40% by weight of an alkaline earth metal fluoride and from 20 to 80% by weight of kieselguhr.

These known catalysts possess insufficient activity and too low a selectivity in hydrogenation of dialkyl dicarboxylates to the corresponding diols.

It is an object of the present invention to prepare a highly active and selective catalyst which permits the hydrogenation of the carboxylates for the preparation of the diols to be carried out in an economical manner, even in a continuous procedure.

We have found that this object is achieved, and that a catalyst which contains copper and silica and has the desired advantages is obtained, if an aqueous alkali metal silicate solution containing from 1.0 to 26% by weight of $SiO_2$ is brought to a pH of from 0.5 to 2.0 with nitric acid, an aqueous copper nitrate solution containing from 5 to 15% by weight of Cu is added, after the addition of the nitric acid, to give a clear solution which contains from 0.18 to 3.0 moles of Cu per mole of $SiO_2$, the resulting solution is mixed with an aqueous alkali metal carbonate solution at from 40° to 80° C., the pH of the mixture being maintained at from 7.5 to 8.5, and the precipitated material is separated off, dried, calcined by heating at from 250° to 400° C. and pressed to catalyst moldings in a conventional manner.

The aqueous alkali metal silicate solution used is advantageously waterglass diluted with water to the desired $SiO_2$ content. The nitric acid is added, for example, in the form of a 20–60% strength acid, after which the copper nitrate solution is added. This starting solution is prepared at from 20° to 40° C., preferably at room temperature. It is important that the silicate solution containing nitric acid is still clear after the addition of the copper nitrate solution.

Advantageously, the copper-containing silicate solution is mixed with the aqueous alkali metal carbonate solution in such a way that the two solutions are combined while stirring, advantageously by introducing them uniformly and simultaneously into initially taken water, the feed being regulated so that a pH of from 7.8 to 8.5 is maintained during the entire precipitation process. The mixture is kept at, for example, from 40° to 80° C. during this procedure. The alkali metal carbonate solution used is, for example, a 5–25% strength by weight sodium carbonate or potassium carbonate solution.

The material precipitated during mixing is separated off and advantageously washed nitrate-free with water. It is then dried in a conventional manner, calcined by heating at from 250° to 400° C., preferably from 300° to 350° C., and pressed to give catalyst moldings. For example, the moldings are prepared by pressing, after the addition of 0.5–2.5% by weight of graphite, and the compressive strength of the moldings should be from 350 to 450 $Kp/cm^3$. It has also proven advantageous for the moldings to be subsequently calcined at from 250° to 350° C., for example from 2 to 5 hours, after the pressing procedure. The catalysts obtainable by the novel process are very useful for hydrogenating the dialkyl dicarboxylates to diols. Examples of suitable dialkyl dicarboxylates are dialkyl esters of $C_4$–$C_6$-dicarboxylic acids, such as succinic acid, glutaric acid and adipic acid, alkyl being of, for example, 1 to 12 carbon atoms. In the hydrogenation of the stated esters for the preparation of the corresponding diols, the catalysts used according to the present invention are superior to the known catalysts in that the former have a higher space-time yield and selectivity.

The dialkyl dicarboxylates are hydrogenated in a conventional manner in a reactor at from 80° to 200° C. and under from 1 to 400, preferably 50 to 300, bar. To do this in practice, the catalyst is installed in the reactor and first reduced by passage of a mixture of nitrogen and hydrogen. This reduction of the catalyst is carried out at, for example, from 100° to 200° C. The hydrogen is metered in at a rate such that a maximum temperature of 230° C. is not exceeded. The catalyst actuated in this manner can be used for hydrogenating the ester.

EXAMPLE 1

In order to prepare the catalyst, the following two solutions are prepared separately:

Solution (a) 2.328 kg of waterglass containing 24.8% by weight of $SiO_2$ are dissolved in 36 l of water, and the pH of the resulting aqueous solution is brought to 2.0 by adding 30% strength nitric acid, while stirring thoroughly. Thereafter, 13.307 kg of an aqueous copper nitrate solution containing 14.4% by weight of copper are added at room temperature. The solution must still be clear after the addition of the copper nitrate.

Solution (b) This solution is prepared by dissolving 5.12 kg of sodium carbonate in 16 l of water.

10 l of water at 60° C. are initially taken in a heatable stirred kettle. Solution (a) and solution (b) are then pumped simultaneously into the stirred kettle in the course of 60 minutes. During this procedure, the temperature is kept at 60° C. and the feed rate is controlled so that the pH of the reaction mixture is maintained at 8.0 during the entire precipitation time. When precipitation is complete, stirring is continued for a further 30 minutes, and the precipitate is filtered off. The filter cake is washed nitrate-free with water and then dried at 110° C. to give 3.8 kg of a dry product having a loss on ignition (2 hours at 900° C.) of 27% by weight. After the drying procedure, calcining is carried out for 7 hours at 300° C. to give 2.9 kg of a calcined product containing 60% of Cu and 18.4% of $SiO_2$ and having a loss on ignition of 5.6% (2 hours at 900° C.). The product is comminuted to a particle size of <1.5 mm, and 1% by weight of graphite is then admixed. The catalyst is then pressed to give 5×5 mm pills.

The compressive strength of the pills should be from 350 to 450 kp/cm². After pressing, the pills are subsequently calcined for a further 4 hours at 300° C. About 2.9 kg of pills having a bulk density of about 1.0 kg/l are obtained.

EXAMPLE 2

The catalyst prepared as described in Example 1 is used as follows:

94 g of the catalyst prepared as described in Example 1 are installed in a 1.5 l stirred autoclave and heated at 100° C. under nitrogen. 1 vol% of hydrogen is then added to the nitrogen. By passing through this gas mixture consisting of 99% by volume of $N_2$ and 1% by volume of $H_2$, the temperature is increased by 20° C. per hour until it reaches 180° C. At this temperature, the catalyst is reduced for a further 12 hours by further passage of the mixture of $H_2$ and $N_2$, and then flushed with nitrogen. The autoclave is then charged with 900 g of dibutyl succinate, and the ester is hydrogenated under the following reaction conditions:

Temperature: 180° C.
$H_2$ pressure: 280 bar
Turbine speed: 2000 rpm.

After 10 and 20 hours, liquid samples were taken from the autoclave and analyzed by means of gas chromatography. The reacted mixture gave the following concentrations:

|  |  | After 10 hours | After 20 hours |
|---|---|---|---|
| Dibutyl succinate, | % by weight | 23 | 3 |
| Butanol | % by weight | 48 | 63 |
| Butanediol | % by weight | 21 | 33 |
| Tetrahydrofuran | % by weight | 0.1 | 0.3 |

EXAMPLE 3

(Comparative example)

Example 2 is repeated, except that the catalyst used comprised 100 ml (139 g) of the catalyst available commercially under the name Girdler 9-13 (shape: 3.5×4.5 mm tablets, composition: 38.6% of Cu, 26.5% of Cr and 0.4% of Mn). The corresponding concentrations in the reacted mixute are:

|  |  | After 10 hours | After 20 hours |
|---|---|---|---|
| Dibutyl succinate, | % by weight | 75 | 66 |
| Butanol | % by weight | 14 | 24 |
| Butanediol | % by weight | 4 | 8 |
| Tetrahydrofuran | % by weight | 0.6 | 1.1 |

The catalyst used in this Example, and its use for the hydrogenation of aliphatic esters, is described by, for example, Charles L. Thomas in Catalytic Processes and proven Catalysts, Academic Press, New York and London, 1970.

EXAMPLE 4

(Comparative example)

Example 2 is repeated, except that the catalyst used comprises 100 ml of the catalyst available commercially under the name R 3-11 (BASF) (shape: 4.5×5.0 mm tablets, composition: 40% of Cu on magnesium silicate).

The corresponding concentrations in the reacted mixture are:

|  |  | After 10 hours | After 20 hours |
|---|---|---|---|
| Dibutyl succinate, | % by weight | 50 | 31 |
| Butanol | % by weight | 27 | 39 |
| Butanediol | % by weight | 10 | 14 |
| Tetrahydrofuran | % by weight | 0.3 | 0.6 |

The results obtained in Examples 2, 3 and 4 are summarized in the Table below.

Space-time yield (g of butanediol per l of catalyst volume per hour) and

Catalyst activity (g of butanediol per kg of catalyst per hour) for the firSt 10-hour experimental period.

Butanediol/tetrahydrofuran ratio after an experimental period of 20 hours.

| Example No. | Space-time yield $(g \cdot l^{-1} \cdot h^{-1})$ | Catalyst activity $(g \cdot kg^{-1} \cdot h^{-1})$ | Butanediol:tetrahydrofuran |
|---|---|---|---|
| 2 | 189 | 239 | 110 |
| 3 | 36 | 26 | 7 |
| 4 | 90 | 115 | 23 |

EXAMPLE 5

51 l of the catalyst prepared as described in Example 1 are installed in the reactor (1) of a circulation apparatus shown schematically in the FIGURE. The apparatus is heated to 100° C., nitrogen (2) being fed in. A mixture of nitrogen and hydrogen (1–2% by volume of $H_2$) is then passed through the apparatus via the feed line (2) in order to reduce the catalyst. Reduction is carried out for 60 hours at 200° C. after which the dibutyl succinate to be hydrogenated is pumped by means of the feed pump (3) from the container (4) to the feed line (2), and is fed into the hydrogenation circulation together with the hydrogen. The temperature is brought to 190° C. with the aid of the heat exchanger (5). By means of level control in the Separator (6), an amount of product corresponding to the feed is removed continuously (7). Product recycling (8) is effected with the circulatory pump (9). The waste gas is removed via the outlet line (10). Hydrogenation of the dibutyl succinate to butanediol is carried out under the following reaction conditions:

$H_2$ partial pressure: 250 bar
Temperature: 190° C.
Amount of waste gas: 1.3 (m³/h)
Liquid circulation: 350 (l/h)
Cross-sectional loading: 35 (m³/m² per hour)

The following results are obtained:

| Space-time yield $\frac{(kg\ of\ butanediol)}{l\ of\ catalyst \cdot hour}$ | 0.17 | 0.24 |
|---|---|---|
| Conversion (%) | 92 | 87 |
| Selectivity (%) | 99 | 99 |

EXAMPLE 6

(Comparative example)

The procedure described in Example 5 is followed, except that the catalyst used is that stated in Example 4. The following results are obtained:

| Space-time yield $\frac{\text{(kg of butanediol)}}{\text{l of catalyst} \cdot \text{hour}}$ | 0.11 | 0.12 |
|---|---|---|
| Conversion (%) | 72 | 48 |
| Selectivity (%) | 97 | 94 |

The two last-mentioned Examples show that the catalyst used according to the invention is considerably superior to the known copper catalyst R3-11 with regard to space-time yield, conversion and selectivity.

We claim:

1. In a process for the preparation of a catalyst containing copper and silica, the improvement which comprises:

bringing an aqueous alkali metal silicate solution containing from 1 to 26% by weight of $SiO_2$ to a pH of from 0.5 to 2.0 with nitric acid, adding an aqueous copper nitrate solution containing from 5 to 15% by weight of Cu only after the addition of said nitric acid, so that a clear solution containing from 0.18 to 3.0 moles of Cu per mole of $SiO_2$ is formed, mixing the resulting solution with an aqueous alkali metal carbonate solution at from 40° to 80° C., the pH of the mixture being maintained at from 7.5 to 8.5, to produce a precipitated material, and then separating off and drying said precipitated material, calcining said material by heating at from 250° to 400° C., adding 0.5 to 2.5% by weight of graphite, and pressing said material after said addition of graphite to give catalyst moldings.

2. A process as claimed in claim 1 wherein said clear solution is mixed with a 5 to 25% strength by weight of alkali metal carbonate solution, the alkali metal being selected from the group consisting of sodium and potassium.

3. A process as claimed in claim 1 wherein said calcining is carried out at a temperature of from 300° to 350° C.

4. The catalyst product obtained by the process of claim 1.

5. The catalyst product obtained by the process of claim 2.

6. The catalyst product obtained by the process of claim 3.

* * * * *

UNITED STATES PATENT AND TRADEMARK OFFICE
CERTIFICATE OF CORRECTION

PATENT NO.  : 4,780,448
DATED       : October 25, 1988
INVENTOR(S) : Franz J. Broecker, Rolf Fischer, Klaus-Dieter Malsch, Wolfgang Reiss, Rolf Schnabel, Hans-Martin Weitz It is certified that error appears in the above-identified patent and that said Letters Patent is hereby corrected as shown below:

IN THE DRAWINGS:

The legend "Abgas" should read --OFF GAS--.

Signed and Sealed this

Eleventh Day of July, 1989

Attest:

DONALD J. QUIGG

Attesting Officer

Commissioner of Patents and Trademarks